United States Patent [19]
Yokota et al.

[11] Patent Number: 5,252,480
[45] Date of Patent: Oct. 12, 1993

[54] HUMAN MONOCLONAL ANTIBODY AND HYDRIDOMA PRODUCING THE SAME

[75] Inventors: Shinichi Yokota, Takarazuka; Hiroshi Ohtsuka, Nishinomiya; Hiroshi Ochi, Toyonaka; Hiroshi Noguchi, Kawanishi; Masazumi Terashima, Ibaraki; Masuhrio Kato, Toyonaka, all of Japan

[73] Assignees: Sumitomo Chemical Company, Limited; Sumitomo Pharmaceuticals Company, Limited, Osaka, Japan

[21] Appl. No.: 349,643

[22] Filed: May 10, 1989

[30] Foreign Application Priority Data

May 10, 1988 [JP] Japan ................. 63-114473

[51] Int. Cl.[5] ............ C12N 5/22; C12N 15/02; C07K 15/28; C12P 21/08
[52] U.S. Cl. .................. 435/240.27; 530/388.4; 435/172.2; 435/70.21
[58] Field of Search .............. 424/1.1, 85, 8, 88, 424/85.8; 530/387-389; 435/7, 70.21, 172.2, 240.27, 92; 935/100, 104, 107, 110

[56] References Cited

U.S. PATENT DOCUMENTS 4,777,136  10/1988  Young ..................... 435/240.27

FOREIGN PATENT DOCUMENTS

| | | |
|---|---|---|
| 0163493 | 12/1985 | European Pat. Off. . |
| 0215131 | 3/1987 | European Pat. Off. . |
| 0217527 | 4/1987 | European Pat. Off. . |
| 0256713 | 2/1988 | European Pat. Off. . |
| 0215131 | 3/1987 | Japan . |
| 8404458 | 11/1984 | PCT Int'l Appl. . |
| 8501659 | 4/1985 | PCT Int'l Appl. . |
| WO86/03754 | 7/1986 | PCT Int'l Appl. . |
| WO88/08135 | 10/1988 | PCT Int'l Appl. . |
| 2185266 | 7/1987 | United Kingdom . |

OTHER PUBLICATIONS

Rowe et al., European Journal of Biochemistry, 132:329–337, 1983.
Coughlin, R. T. et al, J. Immunology, 139(2):557–561, Jul. 15, 1987.
Sadoff et al., Antibiotics and Chemotherapy, 36:134–146, 1985.
Stoll, B. J. et al., IDI, 53:656–662, Sep. 1986.
Yokota et al., Eur. J. Biochem, 167:203–209, 1987.
Yokota et al., "Occurrence of D-Rhamnan as the Common Antigen Reactive Against Monoclonal Antibody E87 in *Pseudomonas aeruginosa* IFO 3080 and Other Strains," *J. Bacteriology* 172:6162–6164, Oct. 1990.
Thompson, K. M., "Human Monoclonal Antibodies," *Immunology Today*, vol. 9 (4), (1988).
Zweerink et al, Infection and Immunity, vol. 56, No. 8, pp. 1873–1879 (Aug. 1988).
Hancock et al, Infection and Immunity, vol. 42, No. 1, pp. 170–177 (Oct. 1983).
Wu et al, 11th International ResCongress and 24th National Meeting of the Reticuloendotherial Society (Oct. 17–21, 1987).
Vale et al, Journal of Clinical Microbiology, vol. 26, No. 9, pp. 1779–1782 (Sep. 1988).
Teng et al, Proc. Natl. Acad. Sci. USA, vol. 82, pp. 1790–1794 (1985).
Rivera et al, Journal of Bacteriology, vol. 171, No. 4, pp. 2244–2248 (Apr. 1989).
Appelmelk et al, Prog. Clin. Biol., 272, pp. 373–382 (1987).
Wu et al, J. Leukocyte Bio. 42(4), p. 393 (1987).
Gaston et al., J. Med. Microbiol., 20(3), pp. vi–vii (1985).

*Primary Examiner*—David L. Lacey
*Assistant Examiner*—Susan L. Futrovsky
*Attorney, Agent, or Firm*—Birch, Stewart, Kolasch & Birch

[57] ABSTRACT

A human monoclonal antibody, which has prophylactic and therapeutic effect to infections diseases caused by *Pseudomonas aeruginosa*, and the epitope of which is located in the outer core moiety of LPS of the microorganism. A hybridoma producing the human monoclonal antibody, and processes for preparing the antibody and hybridoma are also provided.

2 Claims, No Drawings

HUMAN MONOCLONAL ANTIBODY AND HYDRIDOMA PRODUCING THE SAME

The present invention relates to a human monoclonal antibody to *Pseudomonas aeruginosa* (hereinafter referred to as "*P. aeruginosa*"), and its production and use. More particularly, it relates to a human monoclonal antibody, which can recognize an oligosaccharide of an outer core moiety of the lipopolysaccharide of *P. aeruginosa*, which is common to various strains of *P. aeruginosa* of different serotypes, and which shows a binding property to *P. aeruginosa* of two or more serotypes and its use. It also relates to a hybridoma capable of producing the antibody, and a process for the production of the antibody. The human monoclonal antibody of the invention is useful for prevention and treatment of infectious diseases caused by *P. aeruginosa*.

The kinds of bacteria causing infectious diseases, i.e. prophlogistic bacteria, have changed with development and change of clinically used antibiotics. As a result, infectious diseases caused by the bacteria which used to show only low pathogenicity or virulence have increased. Thus, *P. aeruginosa* is currently one of the major pathogenic bacteria causing infectious diseases, of which serious symptoms often lead to patient's death, particularly when their immunity is low due to continuous administration of immunosupressants, suffering from cancer or burns or the like.

Among various preventive or therapeutic methods for bacterial infections, the most prevailing one is chemotherapy by the use of antibiotics or antimicrobial agents. In fact, there have been developed various antibiotics including streptomycin, kanamycin, penicillin, cephalosporin, etc., which are sensitive to almost all Gram-positive bacteria (e.g. Staphylococci) and Gram-negative bacteria (e.g. *E. coli*) and produce a prominent clinical effect. However, there are known only few medicinal products to which *P. aeruginosa* is sensitive. Even those medicinal products act on *P. aeruginosa* only bacteriostatically and not bacteriocidally. Thus, they can prevent the growth of *P. aeruginosa* but do not clinically exhibit any remarkable therapeutic effect.

The other preventive or therapeutic method is antibody therapy comprising administration of immunoglobulin. This method is often performed in association with chemotherapy and nowdays attracts much attention as a substitute for chemotherapy. A serum of high antibody titer can be obtained by active immunization of animals such as horses or rabbit, and antibody therapy can be conducted by administration of such serum. In fact, its remarkable therapeutic effect was proved on experimental infections using various animals. It is known from the cases of diphtheria toxin and viper toxin that antibody therapy using sera originated from animals is quite effective even on human beings. However, introduction of a heterogenous protein obtained from animals into a human body causes such a serious side-effect as anaphylaxis or any other allergic reaction. It is thus highly desired to develop human immunoglobulin having a high antibody titer against bacteria and showing a prominent therapeutic effect on bacterial infections.

Conventional human immunoglobulin preparations are manufactured by collecting blood from healthy persons or bacteria-infected patients, subjecting the blood to fractionation to obtain an immunoglobulin fraction, purifying the immunoglobulin fraction and eliminating agglutinating materials therefrom by addition of ethylene glycol, treatment with protease, sulfonization, DEAE-column chromatography, etc., followed by formulation of the resulting product into intramuscularly or intravenously injectionable preparations. These preparations are advantageous in not causing anaphylaxis or any other side-effect as seen on administration of immunoglobulin originated from animals but they have some drawbacks. One of such drawbacks is that their antibody titer against bacteria is low so that a sufficient therapeutic effect can not necessarily be produced. Another drawback is that a stable supply with a high antibody titer in a large amount is difficult, because they are manufactured using blood collected from healthy persons or bacteria-infected patients and the constant and continuous obtainment of sera having a high antibody titer is quite hard. A further drawback is that they may be contaminated with hepatitis virus (e.g. HB virus), Adult T cell leukaemia virus (ATLV, HTLV), etc., because the blood as the starting material is obtained from a number of unknown persons. In order to overcome these drawbacks, production of a human monoclonal antibody is highly desirable, which is prophylactically and therapeutically useful for bacterial infections and replaceable for conventional human immunoglobulin preparations and mouse monoclonal antibodies.

When an antibody is bound to the surface of a bacterial cell, the phagocytosis of a macrophage on the bacterial cell is accelerated (i.e. acceleration of phagocytosis due to opsonization), or the lysis of the bacterial cell by a complement takes place. As the target antigen at the surface of the bacterial cell of *P. aeruginosa*, there are known lipopolysaccharide (LPS), outer membrane protein, flagellum, pilus, etc.

Sawada et al. reported that a large amount of a mouse monoclonal antibody recognizing the outer membrane protein is required in combatting bacteria as compared with a mouse monoclonal antibody which recognizes LPS (J. Infect. Dis., 150, 570-576 (1984)).

LpS consists of O-polysaccharide which represents O-antigen, an outer core oligosaccharide which is common among species to some extent, an inner core oligosaccharide which is generally common to almost all enterobacteria, and lipid A. The O-polysaccharide antigen which exists at the utmost surface of a bacterial cell, consists of repeating units consisting of 2 to 5 sugar residues and its structure varies to a large extent. The structures of almost all O-antigens of the standard serotype strains of *P. aeruginosa* have already been determined (Acta Microbiol. Hung., 35, 3-24 (1988)).

Because determination of the structure of O-antigen by chemical analysis requires a lot of time and labor, antisera or mouse monoclonal antibodies against the O-antigens from the standard strains are employed for the classification of the strains of *P. aeruginosa*. In other words, an unknown strain of *P. aeruginosa* is classified in accordance with an immunological reactivity with the known antibodies or antisera. This classification is known as a serotype, and typical examples of the serotype classification are as follows: Types 1 to 17 according to the classification by Homma et al (Japan. J. Exp. Med. 44, 1 (1974)); Types 1 to 7 according to the classification by Fisher et al. (J.Bacteriol., 98, 835 (1969)); Types A to M according to the classification by the Serotyping Committee for the Japan Pseudomonas aeruginosa Society (hereinafter referred to as "Japanese Committee") (Japan.J.Exp.Med., 45, 329 (1976)); Types 1 to 17 according to the classification by International Antigenic Typing System (IATS) (Int. J. Syst. Bacteriol., 33, 256-264 (1983)), etc. These classifications and their relationship are shown in Table 1 (Japan.-J.Exp.Med., 46, 329 (1976)).

TABLE 1

Serotype Classification of P. aeruginosa

| Japanese Committee 1976 | Homma et al 1974 | IATS 1983 | Fisher et al 1969 |
|---|---|---|---|
| A | 1 | 3 | — |
| B | 2, 7, 13, 16 | 2, 5, 16 | 3, 7 |
| C | 3 | 8 | 6 |
| D | 4 | 9 | — |
| E | 5 | 11 | 2 |
| F | 6 | 4 | — |
| G | 8 | 6 | 1 |
| H | 9 | 10 | 5 |
| I | 10 | 1 | 4 |
| J | — | 11 | 15 | — |
| K | — | 12 | 13 | — |
| L | — | 14 | — | — |
| M | 15, 17 | — | — |
| — | — | 7, 12, 14, 17 | — |

It is known that the antibody specific to a certain O-antigen shows a strong preventive or therapeutic effect on infections caused by P. aeruginosa of the serotype to which said O-antigen belongs but does not show any effect against P. aeruginosa of any other serotype.

The use of a mixture containing 13 or 17 monoclonal antibodies which are respectively responsible for P. aeruginosa strains of 13 or 17 serotypes would be effective in treating infections caused by any one of the strains. However, preparation of such mixture is very troublesome and the clinical utilization of such preparation is difficult to accomplish from a practical point of view.

Various studies on experimentally-infectioned animals and clinical studies have been made so far, and it was revealed that various antisera and monoclonal antibodies specific to core glycolipid of Gram-negative bacteria are effective in prevention of Gram-negative infections, particularly endotoxin shock (WO 8404458; WO 8501659; EP-A-0174204; JA-A-61-130300; Mutharia et al.: Inf.Immun., 45, 631-636 (1984); Teng et al: Proc. Natl. Acad. Sci., USA, 82, 1790-1794 (1985); Gigliotti & Shenep: J.Inf.Dis., 151, 1005-1011 (1985); Braude et al: J.Inf.Dis., 136 (Suppl), S167-173 (1977); Nellesand Niswander: Inf.Immun., 46, 677-681 (1984); Pollack et al: J. Clin. Invest., 72, 1874-1881 (1983); Young et al: Clin. Res., 30, 522A (1982); Young et al: Clin. Res., 32, 518A (1984)).

The above-mentioned antisera or monoclonal antibodies, which are prepared on the basis of the core glycolipid antigen, bind to various Gram-negative bacteria. This apparently shows that the associated epitope exists in an inner core moiety comprising heptose, KDO, etc., or in lipid A moiety.

Sawada et al obtained a monoclonal antibody recognizing a core antigen of P. aeruginosa (Annual reports of the 21st Meeting of the Japan Pseudomonas aeruginosa Society 16, 1987). However, the experiments with animals revealed that the monoclonal antibody was not effective in protecting experimental animals from the infection, and that the monoclonal antibody against the inner core or lipid A moiety is only weakly effective in protecting animals from the infection.

As stated above, a monoclonal antibody against outer membrane protein as well as conventional antibodies against LPS core is not therapeutically effective although their binding spectra are very broad in P. aeruginosa. On the other hand, a monoclonal antibody to O-antigen has a very limited use because it is effective only to P. aeruginosa having a relevant serotype. Consequently, development of immunoglobulin preparations, which have broader binding spectra and which show a significant preventive and therapeutic effect in P. aeruginosa infections is highly desired.

One resolution for the above subject is to find out an antigen common to all strains of P. aeruginosa and to develop a human monoclonal antibody which recognizes the common antigen and shows broad binding spectra, and which is prophylactically and therapeutically effective to infections caused by P. aeruginosa of various serotypes.

An extensive study has been made to establish a method for producing, on an industrial scale, a human monoclonal antibody effective in prevention and treatment of infectious diseases caused by P. aeruginosa and also a high titer human immunoglobulin preparation containing the monoclonal antibody. The inventors of the present invention have paid special attention to an oligosaccharide moiety of the outer core in LPS which is common to P. aeruginosa, and tried to establish a cell line producing a human antibody recognizing said oligosaccharide moiety by the use of B lymphocytes. As a result of the study, they have now succeeded in obtaining a human monoclonal antibody which specifically recognizes the outer core oligosaccharide having a specific chemical structure and which is effective in prevention and treatment of infectious diseases caused by P. aeruginosa of various serotypes. The monoclonal antibody of the invention is characteristic in binding to strains of P. aeruginosa belonging to serotype A, F, G, H, K and M, and differs from the known serotype-specific monoclonal antibodies which recognize O-antigen polysaccharide and can bind only to the specific strain of P. aeruginosa having the relevant serotype. Further, the monoclonal antibody of the invention also binds to E. coli strain of serotype 026. More specifically, the antigenic determinant or epitope for the monoclonal antibody of the invention positions near rhamnose or galactosamine residue in the outer core moiety of LPS of P. aeruginosa. The monoclonal antibody of the invention is also characteristic in showing prophylactic and therapeutical activity in an experimentally infected mouse.

Known monoclonal antibodies against the core of LPS bind to a variety of Gram-negative bacteria, which suggests that their epitopes are located in the inner core or lipid A moiety of LPS. Prophylactic activities of the known antibodies are relatively low on experimentally infected animals.

As will be understood from the above, the monoclonal antibody according to the present invention is distinctly different from the above-mentioned anti-core glycolipid antibodies in that the former is reactive with the outer core moiety which is common extensively in the strains of P. aeruginosa, and that the former exhibits a remarkable prophylactic and therapeutic effect in experimentally infected animals.

Human monoclonal antibody prepared by Sawada et al (supra), which recognizes a core antigen of P. aeruginosa, binds to 75% of P. aeruginosa of serotype A, 100% of B, 0% of E, 43% of G, 100% of H, and 60% of I, and differs in the binding spectra from the monoclonal antibody of the present invention. Thus, the antibody of Sawada et al apparently recognizes an epitope different from that of the antibody of the invention. On the other hand, the antibody of Sawada et al was shown to exhibit no prophylactic activity in experimentally infected animals. Consequently, the monoclonal antibody of the present invention which recognizes the outer core moiety of LPS of P. aeruginosa is different from the human anti-core monoclonal antibody of Sawada et al.

Accordingly, a primary object of the present invention is to provide a human monoclonal antibody which can recognize an oligosaccharide of the outer core moiety of LPS of P. aeruginosa and bind to strains of P. aeruginosa of various serotype with high frequency, and which is effective in prevention and treatment of infectious diseases caused by P. aeruginosa. Another object of the invention is to provide a human cell line which is capable of producing the monoclonal antibody continuously. A further object of the invention is to provide a high titer immunoglobulin preparations for prevention or treatment of infectious diseases caused by P. aeruginosa, which comprises at least one monoclonal antibody of the invention. A still further object of the invention is to provide processes for the production of the monoclonal antibody and the human cell line. These and other objects of the present invention will be apparent to those skilled in the art from the foregoing and subsequent descriptions in the present specification.

The monoclonal antibody of the invention which recognizes the oligosaccharide of the outer core moiety of LPS of P. aeruginosa is intended to mean a human monoclonal antibody produced by a single antibody-producing clone, which antibody is capable of binding to strains of P. aeruginosa of various serotypes, particularly serotypes A, G, F, H, K and M, with high frequency.

The monoclonal antibody of the invention can be prepared, for example, by the following procedures.

Human B lymphocytes sensitized with (1) P. aeruginosa (living bacteria or bacteria killed by formalin or heat), or (2) R mutant of P. aeruginosa which has no O-antigenic polysaccharide, or (3) preferably LPS derived from the R mutant, is subject to cell fusion with a myeloma cell or a B lymphoblastoid cell, and the resultant hybridoma is allowed to grow continuously in vitro, whereby a cell line capable of continuously producing the desired antibody is established. The established cell line is cultured in vitro, and the antibody secreted in the culture medium is extracted and purified to obtain the desired antibody in large quantities.

The serotype used herein is in accordance with the Classification pursuant to the Japanese Commitee, which is determined on the difference in immunological reaction using an antiserum or a mouse monoclonal antibody specifically reactive to the standard strain of P. aeruginosa of each serotype.

LPS stands for a lipopolysaccharide and constitutes a major component of an outer membrane of Gram-negative bacteria. LPS consists of (1) a glycolipid called lipid A, (2) an inner core oligosaccharide comprising 2-keto-3-deoxyoctonic acid, heptose, ethanolamine, phosphate, etc. as its constituents, (3) an outer core oligosaccharide of which constituents differ depending on species and which comprises, as far as P. aeruginosa is concerned, glucose, rhamnose, galactosamine, alanine, etc. as its constituents, and (4) a polysaccharide called O-antigen which determines the serotype, said lipid A being tied up with said inner and outer core moieties and said O-antigen being tied up with said outer core moiety.

The outer core oligosaccharide of LPS, which constitutes an antigen common to many strains of P. aeruginosa, is located at the place to which the O-polysaccharide is attached. Thus, the outer core oligosaccharide appears to be positioned next to the O-polysaccharide which is located at the utmost outside of the bacterial cell surface.

It is known that the chemical structure and composition of the outer core oligosaccharide vary depending on strains (Wilkinson, Rev. Infect. Dis. 5, S941–S949 (1983)). However, the constituents of the oligosaccharide are common to many strains of P. aeruginosa and comprise glucose, rhamnose, galactosamine, alanine, etc. as major components.

The term "monoclonal antibody" herein used means an antibody which has a uniform molecular structure and which is produced by a single antibody-producing clone which, in turn, can be obtained by a cell fusion (Nature, 256, 495 (1975)) or EB virus transformation (Proc. Natl. Acad. Sci. USA., 70 190 (1973)).

Production of the human monoclonal antibody of the invention comprises the following steps: (1) preparation of human B lymphocytes sensitized with an antigen; (2) establishment of the cell line which produces specific monoclonal antibody by immortalizing the cells as prepared in (1); (3) cultivation of the cell lines as established in (2); (4) purification of the monoclonal specific antibody from the culture as obtained in (3); and (5) production of an immunoglobulin preparation of high titer comprising the monoclonal specific antibody as purified in (4). Each of these steps will be hereinafter explained in detail.

Step (1)

As the human B lymphocytes, there may be used human lymphocyte cells producing an antibody to the outer core oligosaccharide of LPS of P. aeruginosa, which can be separated from peripheral blood by the centrifugation using a lymphocyte separation liquid such as Lymphoprep ® or Mono-Poly Resolving Medium ® (Flow Lab.). There may be also used B lymphocytes originated from tissues or organs (e.g. lymph node, spleen) extracted for the purpose of diagnosis or therapy of diseases, umbilical cord blood or the like. It is desirable to obtain the cells from persons who were infected with P. aeruginosa in the past and whose cells are sensitized by the infection. Suitable persons, from whom the cells may be obtained, can be chosen by previous measurement of the antibody titer in their sera which has been raised against formalin-treated P. aeruginosa cell or LPS derived from P. aeruginosa. Alternatively, human B lymphocytes may be obtained from any person irrespective of his medical history in the past. Such lymphocytes are mixed with formalin-treated P. aeruginosa, or preferably LPS derived from P. aeruginosa, before use for cell fusion. Namely, P. aeruginosa killed by formalin-treatment or, preferably, LPS of P. aeruginosa is added to B lymphocytes as an antigen. Further, solutions containing lymphokines such as B cell proliferation factors and B cell differentiation factors (e.g. plant lectins such as pokeweed mitogen (PWM), bacterial components such as Cowan I, human lymphocyte mixed culture, spleen, thymus or umbilical cord blood cell culture) may be added to human B lymphocytes for sensitization in vitro, followed by profileration and differentiation to give antibody-producing cells. The thus obtained human B lymphocytes have an antibody molecule at the cell surface an can release a small amount of antibody for a certain limited period but they are not immortal.

Step (2)

For changing the above sensitized human B lymphocytes to continuously proliferable immortal cell lines, the sensitized human lymphocytes and myeloma cells are subjected to cell fusion in the presence of polyethylene glycol. The myeloma cells as used are hypoxanthine-guanine phosphoribosyl transferase (HGPRT)-deficient mutants (e.g. P3X63-Ag 8 (P3), P3X63-Ag 8.653) originated from mouse myeloma cell, HGPRT-deficient mutant originated from human myeloma cell U-266, HGPRT-deficient mutants originated from mouse-human heteromyeloma cell which is obtained by cell fusion between mouse myeloma cell and human myeloma cell, or mouse myeloma cell such as SHM D-33 and human lymphocyte B cell. HGPRT-deficient mutants originated from human B lymphoblastoid cell can be used in place of myeloma cell.

As the polyethylene glycol (PEG), there may be used, for instance, PEG 1,000 to 6,000 in a concentration of 30 to 50% (w/v). The fusion efficiency can be enhanced by incorporation of lectin, poly-L-lysine, dimethylsulfoxide, etc. thereto.

The fusion may be carried out, for instance, in the same manner as described in the Köhler et al. article (Nature, 256, 495 (1975)) wherein mouse cells are fused each other to obtain a hybridoma producing a mouse monoclonal antibody. For instance, the sensitized human lymphocytes and HGPRT-deficient myeloma cells or human-mouse heteromyeloma cells are mixed together in a proportion of 3-1:1, and 45% (w/v) PEG 1500-6000 is added portionwise thereto in 0.5 to 1 minute, and the resultant mixture is allowed to stand for 0.5 to 3 minutes. To the resulting mixture, 10 to 50 ml of a culture medium containing no serum are added in 5 to 10 minutes, and subsequently 2 ml of FCS are added, and the mixture is incubated at 37° C. for 10-60 minutes. After centrifugation, fresh culture medium is further added thereto to make a cell concentration of $10^5$ to $10^6$/ml. The cell suspension thus obtained is inoculated into a 96 well microplate at a rate of $2\times10^4$ to $2\times10^5$ cells per well. On the next day, half the amount is replaced by a hypoxanthine-aminopterin-thymidine-containing medium (HAT medium) or a hypoxanthine-azaserine-containing medium (HAz medium), and cultivation is effected at 32° to 37° C. under 5% $CO_2$. For about 10 to 20 days, the culture medium is replaced by HAT medium or HAz medium, and subsequently by hypoxanthine-thymidine-containing medium (HT medium) or hypoxanthine-containing medium (H medium) for about 3 to 5 days. The replacement was done on half amount basis at intervals of 3 days for 2 or 3 weeks to obtain a proliferative colony, i.e. hybridoma. It is also possible to select a hybridoma by the combined use of metabolism inhibitors without using a HGPRT-deficient mutant.

The antibody titers of the culture medium against seventeen strains of P. aeruginosa killed by formalin-treatment or against their LPS, said strains constituting seventeen serotype panel, is measured by ELISA or radioimmunoassay, and the desired cell which produces the specific antibody to the outer core moiety of LPS of P. aeruginosa is selected with the aid of the Western blotting method. Cloning is repeated two or three times by the limiting dilution method or the agarose method to obtain a stable cell line having a high rate proliferative property and a high specific antibody productivity.

The cell lines as established from sensitized human B lymphocytes according to the cell fusion (hybridoma) method can be proliferated continuously and produce the specific antibody stably in a large amount.

Step (3)

The thus established hybridomas $(0.5-5\times10^5$ cells/ml) are cultured in a settled culture or spinner culture using a usual culture medium for animal cells in a vessel such as a cell culture flask or plate by the use of a $CO_2$ incubator at 32° to 37° C. under 2 to 10% $CO_2$. Particularly when culture is made at a large scale, a jar fermenter, a hollow fiber system or the like designed for animal cells may be used. The usual culture medium may be, for instance, a medium (e.g. RPMI1640, Eagle's MEM) containing 2 to 20% serum of bovine fetus, calf, cow, horse, human or the like, a serum-free medium containing supplements required for the growth of cells (e.g. insulin, transferrin, ethanolamine, selenite, bovine albumin, lipid) or the like.

Cultivation of the hybridoma may also be conducted, in place of the in vitro cultivation mentioned above, by intraperitoneally inoculating and cultivating the hybridoma in animals such as a nude mouse. When a mouse or a nude mouse is employed, 0.5 to $2.5\times10^7$ cells per mouse are inoculated. It is preferred to administer pristane or anti-asialo $GM_1$ antibody before inoculation. Radiation of X-ray or spleen extraction may also be helpful for successful inoculation.

Step (4)

Purification of the antibody may be carried out by conventional biochemical procedures (e.g. ammonium sulfate precipitation, ethanol precipitation, PEG fractionation, ion exchange chromatography, gel filtration, affinity chromatography, high performance liquid chromatography, electrophoresis). In the purification process, care should be taken for preventing the production of agglutination or the depression of antibody activity. For this purpose, human serum albumin (HSA) may be added in an amount of 0.05 to 2%. Addition of amino acids such as glycine or alanine, especially basic amino acids such as lysine, arginine or histidine, carbohydrates such as glucose or mannitol, salts such as sodium chloride, etc. may be sometimes preferred. Agglutination tends to be produced, particularly in the case of IgM antibody, and treatment with β-propionolactone, acetic anhydride or the like is effective in prevention of such agglutination In such case, intravenous administration will be made possible.

Step (5)

The purified monoclonal antibody may be formulated into a biological preparation by a per se conventional procedure comprising, for instance, filtering through a membrane filter for removal of bacteria, admitting into sterilized vials with stabilizers and lyophilizing.

The human monoclonal antibody preparation of the invention may comprise only one kind of human monoclonal antibody to the outer core moiety of LPS of P. aeruginosa for its use as a preventive or therapeutic agent for infections with P. aeruginosa. Preferably, the preparation comprises additionally at least one kind of human monoclonal antibody which can recognize a different epitope of a different chemical structure in the outer core oligosaccharide of LPS of *P. aeruginosa*.

The preparation may also contain a human monoclonal antibody which can recognize any of other surface antigens of *P. aeruginosa* such as O-antigen, outer membrane proteins, flagellum, and pilus, pathogenic factors of *P. aeruginosa*, such as exotoxins, or exoenzymes such as elastase and proteases. The preparation of the invention may be employed after being combined with any conventional human immunoglobulin preparation. The preparation may also be employed after being combined with any human monoclonal antibody to bacteria other than *P. aeruginosa*, virus, fungi, protozoa, cancer cells, and any conventional human immunoglobulin preparation. On the other hand, the human monoclonal antibody of the invention may be incorporated into a conventional human immunoglobulin preparation to make a high titer immunoglobulin preparation to *P. aeruginosa*.

The human monoclonal antibody of the present invention binds to the surface of *P. aeruginosa* cells, particularly to the outer core moiety of the LPS of the cell surface which constitutes an antigen common to many strains of *P. aeruginosa*. The binding of the antibody leads to the opsonization of the *P. aeruginosa* cell which enhances phagocytosis and bacteriolysis actions of phagocytes on the cell and activation of complements which accelerates the lysis of the cell. Accordingly, experimental mouse infections with *P. aeruginosa* can be treated by administration of the human monoclonal antibody of the invention.

For prevention and treatment of infectious diseases with *P. aeruginosa* or infections by bacteria containing *P. aeruginosa*, the human monoclonal antibody of the invention may be administered to an adult patient in an amount of about 0.5 to 500 mg, preferably 5 to 50 mg.

As stated above, the major advantageous merits of the human monoclonal antibody of the invention is that it has a high antibody titer to its antigen and shows an excellent therapeutic effect in the system of experimental mouse infections and that it is effective to various *P. aeruginosa* of different serotype. Other merits of the antibody of the invention are as follows.

Since it is a human-origin protein, any side effect (e.g. anaphylaxis) as seen on the administration of a heterogenic protein does not occur. Since it is produced from a certain specific cell line, a possibility of contamination with unknown biohazardous materials is much less in comparison with conventional immunoglobulins prepared from human blood obtained from a number of unknown persons. The human monoclonal antibody of the invention is produced with a high antibody titer in vitro stably in a large amount, and its production process is more advantageous than conventional production processes using human blood in easy quality control.

The present invention will be hereinafter explained in details by way of examples, but it should be understood that this invention is not limited to those examples.

EXAMPLE 1

Establishment of Human Monoclonal Antibody MH-4H7-Producing Cell Line Prepared by Human-Mouse Cell Fusion (1) Preparation Of Human Lymphocytes From Peripheral Blood And Its Cultivation Peripheral blood (100 ml) having a high antibody titer against *P. aeruginosa* surface antigens was taken from a healthy volunteer (donor). To a centrifuge tube (50 ml, Sumitomo Bakelite) was added Mono-Poly Resolving Medium ® (Flow Lab.), and peripheral blood (20 ml) was slowly overlaid thereon, followed by centrifugation with a low speed centrifuge (BS-20BH, Tommy Precision Ind.) at 1,500 rpm and (Roter-TS-7) at room temperature for 30 minutes, whereby erythrocytes and lymphocytes were separated.

The portion containing lymphocytes was collected and washed three times with a Dulbecco's modified Eagle's Minimum Essential Medium (hereinafter referred to as D-MEM), followed by calculation of the cell numbers to obtain lymphocyte cells $1.2 \times 10^8$.

The lymphocyte cells ($6 \times 10^7$) were suspended in a lymphocyte-culturing medium (66 ml) containing formalin-killed cells of *P. aeruginosa* (IID1001 (Type A) & IID1020 (Type G), each 0.0002%), and the suspension was dispensed in 24 well microplates (Costar, #3424) at a rate of $1.5 \times 10^6$ lymphocyte cells/well and cultured at 37° C. under 5% $CO_2$ for 6 days. The lymphocyte-culturing medium just mentioned means RPMI-1640 medium which contains 20%(v/v) of inactivated fetal calf serum (FCS), 0.05 mg/ml of sodium pyruvate, $5 \times 10^{-5}$M of 2-mercaptoethanol, 30 μg/ml of transferrin derived from calf plasma (United States Biochemical Corp.) and 0.01%(v/v) of plant lectin derived from pokeweed (Gibco Lab.).

(2) Cell Fusion

Human-mouse heteromyeloma cells (SHM-D33, ATCC No. CRL1668) were subcultured in D-MEM containing 15% FCS, and $2.5 \times 10^7$ cells were washed twice with D-MEM.

On the other hand, peripheral blood lymphocytes cultured for 6 days in 24 well microplates according to Example 1-(1) were recovered to give $7.4 \times 10^7$ lymphocyte cells. The cells were washed with D-MEM three times and mixed with the above human-mouse heteromyeloma cells in a centrifuge tube, followed by centrifugation to give precipitates.

To the precipitates in the centrifuge tube was added 1 ml of a polyethyleneglycol (PEG) solution (0.45 g of PEG4000 (Merck), 0.45 ml of PBS(—), and 0.1 ml of dimethylsulfoxide) in about one minute under rolling of the tube, and the mixture was left to stand at room temperature for one minute. D-MEM was then added to the tube at a rate of 2 ml/minute under rolling of the tube, which was repeated four times. By the use of D-MEM containing 10% FCS rather than D-MEM, the above procedure was repeated three times. Finally, 1.5 ml of FCS was added to the tube, and the mixture was left to stand for 20 minutes at 37° C. The cells were collected by centrifugation and suspended in 40 ml of D-MEM medium containing FCS (15%), sodium pyruvate (0.05 mg/ml), insulin (0.2 U/ml), oxaloacetic acid (0.15 mg/ml), azaserine (1 μg/ml), and hypoxanthine (100 μM), said medium being referred to as "HAz selective medium" hereinafter. The suspension was dispensed in 96 well microplates (Falcon #3040) at a rate of 100 μl per plate so that one well may contain $6.5 \times 10^4$ myeloma cells. Each of the wells of the microplates had previously been charged with 100 μl of the suspension against the aforementioned medium so that each well may contain mouse BALB/c spleen cells ($1 \times 10^5$) and mouse BALB/c peritoneal exudate cells ($1 \times 10^4$), and the plates had been incubated at 37° C. for one day under 5% $CO_2$. The microplates were incubated at 37° C. under 5% $CO_2$ and the half of the culture medium was replaced by HAz selection medium at 2 or 3 day intervals. After one week, half of the culture medium was replaced by H-medium which corresponds to azaserin-free HAz selective medium. After that, half of the medium was replaced by azaserin and hypoxanthine-free hybridoma-culturing D-MEM medium, which is D-MEM medium containing FCS (15%), sodium pyruvate (0.05 mg/ml), insulin (0.2 U/ml), and oxaloacetic acid (0.15 mg/ml), at 2 or 3 day intervals. Production of antibody to *P. aeruginosa* surface antigen was determined by enzyme linked immuno-sorbent assay (ELISA) on culture supernatants of the wells which showed growth of the cells at the time of three weeks after the cell fusion, by the use of 96 well microplates (Falcon #3912) on which *P. aeruginosa* was fixed by glutaraldehyde. The standard strains of *P. aeruginosa* of seventeen different serotype according to Homma's classification were employed in the above test, which are obtainable from the Institute of Medical Science, Tokyo University, Japan, or from ATCC. The test revealed that one well produced IgM antibody which extensively reacts with plural standard strains of *P. aeruginosa* of different serotypes. The heterohybridoma in the well was further cultivated and cloned by means of the limiting dilution, whereby a cell line designated MH-4H7, which stably produces human IgM antibody, was obtained. The term "MH-4H7" may also be herein used as the name of the human monoclonal antibody produced by the cell line MH-4H7. The hybridoma MH-4H7 was deposited under accession number FERM P-9996 on Apr. 19, 1988 at Fermentation Research Institute, Agency of Industrial Science and Technology, located at Tsukuba, Ibaraki-ken, Japan, and then such deposition was converted to the deposition under Budapest treaty and assigned new accession number FERM BP-2402 on Apr. 26, 1989. The human monoclonal antibody MH-4H7 was IgM ($\mu$, $\lambda$).

A similar IgM-producing hybridoma to the above was obtained from another donor, of which serum showed high antibody titer to *P. aeruginosa* surface antigen, by the separation of lymphocytes, the activation of specific B cells in vitro, and cell fusion as mentioned above.

EXAMPLE 2

Study on Binding Spectrum of Human Monoclonal Antibody MH-4H7 by ELISA (1) Measurement of Anti-*P. aeruginosa* Antibody by ELISA The antibody titer against *P. aeruginosa* surface antigen was measured as follows. *P. aeruginosa* was suspended in a phosphate buffered saline (pH 7.2; comprising NaCl (8 g/l), KCl (0.2 g/l), $NaHPO_4.12H_2O$ (2.99 g/l and $KH_2PO_4$ (0.2 g/l)) (PBS) to give absorbance of 0.2 at a wavelength of 600 nm. The suspension was charged in 96 well microplates (Falcon #3912) at a rate of 50 µl/well, followed by centrifugation at 2,000 rpm for 15 minutes. 2% Glutaraldehyde was added to each well at a rate of 50 µl/well to fix the bacterial cell to the microplate. After removal of the bacterial suspension from the microplates, 3% PBS solution containing bovine serum albumin (BSA) was charged to the microplate at a rate of 120 µl/well and incubated at 37° C. for 30 minutes for blocking of the unbound portion of the assay plate. The resulting microplate was used as the antigen-coated plate in the subsequent operations. When desired, storage of such microplate may be made at −20° C.

Prior to the assay, the microplate was washed with a 0.05% Tween 20 containing PBS solution (PBST) three times. PBST was charged into wells at a rate of 50 µl/well, and a sample (serum, ascites or culture supernatant), optionally diluted with PBS, was added thereto at a rate of 50 µl/well, followed by incubation at 37° C. for 2 hours. The sample was removed from the plate, which was washed with PBST three times. Alkaline phosphatase-conjugated affinity purified goat anti-human immunoglobulin antibody (Kirkegaard & Perry Lab. Inc.) (secondary antibody) diluted with 1% BSA containing PBS solution in 500 to 1,000 folds was added to the microplate at a rate of 100 µl/well for incubation at 37° C. for 2 hours. For measurement of the IgG antibody titer and the IgM antibody titer, there were respectively employed alkaline phosphatase-conjugated goat anti-human IgG antibody and alkaline phosphatase-conjugated goat anti-human IgM antibody. After removal of the secondary antibody, the microplate was washed with PBST three times, and a substrate solution, i.e. an aqueous solution containing sodium p-nitrophenylphosphate (3 mg/ml) in 10% diethanolamine buffer (pH, 9.1) containing $NaN_3$ (0.2 mg/ml) and $MgCl_2.6H_2O$ (0.1 mg/ml), was added to the microplate at a rate of 100 µl/well, followed by reaction at 37° C. The binding activity of the antibody ($OD_{405}$) was measured on MULTISKAN ® (Titertek).

(2) Binding Property of MH-4H7 to Serotype Standard Strains of *P. aeruginosa*

The binding property of MH-4H7 to the serotype standard strains of *P. aeruginosa* was examined by ELISA as described in Example 2-(1). The strains were obtained from the Institute of Medical Science, Tokyo University, Japan, and cultivated in heart infusion agar medium. The test results are shown in Table 2.

TABLE 2

Binding Activity of MH-4H7 to Serotype Standard Strains of *P. aeruginosa* according to The Japanese Committee's Classification

| Serotype | Strain | ELISA Value |
|---|---|---|
| A | IID 1001 (ATCC27577) | 1.78 |
| B | IID 1002 (ATCC27578) | 0 |
| B | IID 1007 (ATCC27583) | 0 |
| B | IID 1013 (ATCC27589) | 0 |
| B | IID 5004 | 0 |
| C | IID 1021 | 0 |
| D | IID 1004 (ATCC27580) | 0 |
| E | IID 1130 | 0 |
| F | IID 1006 (ATCC27582) | 1.77 |
| G | IID 1008 (ATCC27584) | 1.88 |
| G | IID 1020 | 1.98 |
| H | IID 1009 (ATCC27585) | 1.33 |
| I | IID 1010 (ATCC27586) | 0 |
| J | IID 1011 (ATCC27587) | 0 |
| K | IID 1012 (ATCC27588) | 1.80 |
| L | IID 5141 | 0 |
| M | IID 5018 | 0 |
| M | IID 1015 | 0 |

The table shows that MH-4H7 was bound selectively to the serotype standard strains of Types A, F, G, H, and K of *P. aeruginosa*.

(3) Binding Property of MH-4H7 to Clinical Isolates

It was shown in the above test that MH-4H7 can bind to the serotype standard strains of Types A, F, G, H, and K. Consequently, binding property of MH-4H7 to several clinical isolates of these serotypes, as well as of Types B, E, I and M which are clinically isolated with high frequency, was examined. As the result, MH-4H7 was bound to Type A clinical isolates (70%), Type F (80%), Type G (86%), Type H (60%), Type K (75%), and Type M (45%) as shown in Table 3. Types B, E, and I clinical isolates (20 strains each) did not bind to MH-4H7.

TABLE 3

Binding Activity of MH-4H7 to Clinical Isolates

| Serotype | Strain | ELISA Value (OD$_{405}$) |
|---|---|---|
| A | sp 6745 | 0.53 |
| | sp 6746 | 1.46 |
| | sp 6783 | 1.10 |
| | sp 6818 | 2.03 |
| | sp 6830 | 0.13 |
| | sp 6840 | 1.17 |
| | sp 6708a | 1.82 |
| | sp 9710 | 1.67 |
| | sp 9711 | 1.07 |
| | sp 9731 | 0 |
| | sp 9762 | 0 |
| | sp 9763 | 0 |
| | sp 9768 | 1.26 |
| | sp 9780 | 1.75 |
| | sp 10029 | 0.33 |
| | sp 10040 | 0 |
| | sp 10060 | 0.39 |
| | sp 10648 | 1.78 |
| | sp 10676 | 0 |
| F | sp 6770 | 2.15 |
| | sp 6771 | 0 |
| | sp 6808 | 0.49 |
| | sp 6851 | 2.24 |
| | sp 6921 | 1.53 |
| G | sp 9701 | 2.23 |
| | sp 9709 | 2.31 |
| | sp 9712 | 0 |
| | sp 9714 | 2.29 |
| | sp 9717 | 0.06 |
| | sp 9718 | 2.28 |
| | sp 9738 | 2.23 |
| | sp 9785 | 1.29 |
| | sp 9743 | 2.31 |
| | sp 9792 | 1.98 |
| | sp 9755 | 2.26 |
| | sp 9761 | 0 |
| | sp 9767 | 2.45 |
| | sp 9772 | 2.33 |
| | GN 11187 | 2.44 |
| | TL 2378 | 2.33 |
| | TL 2424 | 2.43 |
| | sp 6788 | 2.44 |
| | sp 9728a | 2.44 |
| H | sp 6896 | 0 |
| | sp 6931 | 0 |
| | sp 7503 | 2.23 |
| | sp 7507 | 2.44 |
| | sp 7514 | 2.42 |
| | sp 7520 | 2.40 |
| | sp 7522 | 0 |
| | sp 7532 | 0 |
| | sp 7555 | 2.42 |
| | sp 10054 | 0 |
| | sp 10068 | 0.04 |
| | sp 10678 | 2.06 |
| | sp 10681 | 1.71 |
| K | sp 9751 | 1.96 |
| | sp 7861 | 0.06 |
| | sp 7873 | 1.96 |
| M | sp 9716 | 0 |
| | sp 9730 | 0 |
| | sp 9744 | 0.03 |
| | sp 9748 | 0 |
| | sp 9749 | 0.44 |
| | sp 9752 | 0 |
| | sp 9775 | 0 |
| | sp 10067 | 2.19 |
| | sp 10675 | 0 |
| | sp 6763 | 2.29 |

TABLE 3-continued

Binding Activity of MH-4H7 to Clinical Isolates

| Serotype | Strain | ELISA Value (OD$_{405}$) |
|---|---|---|
| | sp 6764 | 2.24 |
| | sp 6765 | 2.22 |
| | sp 6782 | 0.85 |
| | sp 6794 | 0.59 |
| | sp 6833 | 0 |
| | sp 6852 | 2.31 |
| | sp 6890 | 0 |
| | sp 6892 | 2.15 |
| | sp 6895 | 0 |
| | sp 6908 | 1.02 |

EXAMPLE 3

Study on Agglutination Activity of Human Monoclonal Antibody MH-4H7 to Serotype Standard Strains of *P. aeruginosa*

Agglutination activity of MH-4H7 on formalin-treated serotype standard strains of *P. aeruginosa* was measured and expressed by a minimum agglutinating concentration of the antibody. Each of the standard strains listed in Table 4 was cultured on heart-infusion agar medium, treated with 1% formalin, and allowed to stand at 37° C. overnight. The resulting killed cells were suspended in PBS(−) so as to give absorbance of 0.2 at a wavelength of 600 nm, and 50 μl portions of the suspension were charged in U-shaped 96 well microplates (Sumitomo Bakelite). To the plates, MH-4H7 solutions (50 μl each) in 2 fold serial dilutions were added. As a control, solutions containing a human monoclonal antibody, i.e., anti-B type hMcAb (IgM) which recognizes O-antigen of Type B, were added instead of MH-4H7 solutions. The reaction mixtures were left to stand overnight at 4° C., and the presence or absence of agglutination was examined. The results are shown in Table 4.

TABLE 4

Minimum Agglutinating Concentration of MH-4H7

| Antibody | Strains (Serotype) | Minimum Agglutinating Concentration |
|---|---|---|
| MH-4H7 | IID 1001 (A) | 2.5 μg/ml |
| | IID 1006 (F) | 2.5 |
| | IID 1020 (G) | 5.0 |
| | IID 1009 (H) | 2.5 |
| | IID 1012 (K) | 1.25 |
| | IID 1002 (B) | n.d.* |
| anti-B type hMcAb | IID 1002 (B) | 1.25 |

*n.d.; >25 μg/ml

MH-4H7 showed agglutinating activity to binding-positive strains determined by ELISA (Table 2) of the same magnitude as anti-B type hMcAb to the strain of serotype B, although the magnitude somewhat differs from strain to strain.

EXAMPLE 4

Characterization of Recognizing Site of Human Monoclonal Antibody MH-4H7 by Western Blotting Analysis (1) Western Blotting Analysis of Lipopolysaccharide Lipopolysaccharides were collected from serotype standard strains of *P. aeruginosa*, IID1001 (Type A) and IID1020 (Type G), according to the method described by Westphal & Jann (Methods Carbohydr. Chem., 5 83–91 (1965)). Thus, *P. aeruginosa* was cultured to the late exponential phase in heart-infusion broth medium (Nisuui Pharmaceuticals), and the cells were collected by centrifugation. The wet cells were treated with 45% phenol at 68° C. and centrifuged at 3,000 rpm for 15 minutes at temperature of 10° C., whereby lipopolysaccharides were extracted in an aqueous layer. The aqueous layer was treated with cetyltrimethylammonium bromide to remove nucleic acids and precipitated with ethanol to give lipopolysaccharides.

The lipopolysaccharides obtained from IID1001 and IID1020 were each treated with a sample buffer comprising Tris buffer (31 mM), pH6.8, SDS (1.5%), glycerol (5%), mercaptoethanol (2.5%), and Bromphenol blue (0.005%) at 100° C. for 5 minutes, subjected to electrophoresis on 12.5% polyacrylamide gel containing 0.2% SDS, and transferred to DURAPORE® filter (Millipore). On the membrane, the binding site of human monoclonal antibody MH-4H7 was identified by enzyme-labeled antibody coloring method employing alkaline phosphatase-conjugated goat anti-human IgM antibody (Kirkegaard & Perry Lab. Inc., Gaithersburg, Md.). As detecting phoretic pattern of LPS, the same test sample was electrophoresed in the same manner, and the gel was developed by silver staining using Bio Rad kit.

The silver staining showed in higher molecular weight region the presence of a group of bands in ladder shape due to smooth type LPS which contains O-polysaccharide. The characteristic bands are attributable to heterogeneity of the numbers of the repeating unit of the O-polysaccharide. Single broad band or a few bands observed in lower molecular weight region is assigned to LPS of R type or SR type which lacks O-polysaccharide or which has only a few repeating units.

As the results, a strong color-development was observed in both strains of IID1001 and 1020 at the position of lipopolysaccharides of R type or SR type, which lacks O-polysaccharide altogether or has a short O-polysaccharide. Positive reaction with MH-4H7 was not observed and only slight color development was observed in the region corresponding to the bands in ladder shape detected by the silver staining which comprise smooth type LPS having O-polysaccharide repeating structure.

(2) Western Blotting Analysis of SDS-treated Cells

Western blotting was conducted on SDS-treated cells of serotype standard strains of P. aeruginosa, IID1001 (Type A), IID1006 (Type F), IID1008 (Type G), IID1020 (Type G), IID1009 (Type H), and IID1012 (Type K). The cells were each grown in heart-infusion broth medium, suspended in the sampling buffer described in Example 3-(1), and subjected to SDS-treatment at 100° C. for 30 minutes. The sample thus obtained was electrophoresed on 12.5% polyacrylamide gel containing 0.2% SDS, with the application amount of the sample corresponding to 2 mg of the wet cells, and transferred to DURAPORE® filter in the same manner as in Example 3-(1). The enzyme-labeled antibody coloring was conducted on this filter. In each strain, color development by the action of MH-4H7 was observed only in the region corresponding to R type or SR type lipopolysaccharide, and the region of higher molecular weight gave no color development.

EXAMPLE 5

Separation and Fractionation of Polysaccharide and Lipid A Portions of LPS of P. aeruginosa and Study on Binding Properties of Resultant Fractions to Human Monoclonal Antibody MH-4H7

(1) Separation of Polysaccharide Portion of LPS of P. aeruginosa IID1001

According to Wilkinson & Glbraith's method (Eur. J. Biochem., 52, 331 (1975)), polysaccharide portion was separated from LPS of P. aeruginosa IID1001 and the polysaccharide obtained was fractionated. Namely, LPS (10 mg) was dissolved in 1% acetic acid and heated at 100° C. for 90 minutes to selectively hydrolyze the ketosidic linkage in 2-keto-3-deoxyoctonate (KDO) residue present in the inner core of LPS. The reaction mixture was extracted with chloroform to obtain lipid A preparation. For fractionation, the mother liquid from which free lipid A had thus been removed was subjected to Sephadex® G-50 column chromatography (Pharmacia, Uppsala) (column size: 1×70 cm) equilibrated with 50 mM pyridine/acetate buffer, pH 5.5. Elution of O-polysaccharide, SR core oligosaccharide, and R core oligosaccharide was detected by the colorimetric determination described hereinafter.

Neutral sugars were detected by the phenol-sulfuric acid method (M. Dubois. et al., Anal. Chem. 28, 350 (1956)). Amino sugars were detected by hydrolyzing the sample with 2N $H_2SO_4$ at 100° C. for 2 hours and subjecting the hydrolyzed product to MBTH (3-methyl-2-benzothiazolinone hydrazone hydrochloride) method (A. Tsuji et al., Chem. Pharm. Bull., 17 217 (1969)). The polysaccharide, and the core-oligosaccharides of R type and SR type were recovered by lyophilization of the relevant fractions.

(2) Binding Property of MH-4H7 to Each Fraction Derived From Lipopolysaccharide

Competitive reaction in ELISA was used for studying the binding property of MH-4H7 to respective fractions containing the polysaccharide, the SR core oligosaccharide, the R core oligosaccharide, and the lipid A originated from P. aeruginosa IID1001, which were all obtained in Example 4-(1). Thus, a mixture of the competitor and the antibody was incubated at 37° C. for one hour and subjected to ELISA using 96 well microplates on which P. aeruginosa cells had been coated, whereby the rate of inhibition was measured. The amount of the competitors were the ones corresponding to 100 nmol of the neutral sugars according to the phenol-surfuric acid determination mentioned in Example 4-(1). The results are shown in Table 5.

TABLE 5

| Binding Property of MH-4H7 to Fractions of Polysaccharide and Core Oligosaccharides of R Type and SR Type | |
|---|---|
| Competitive Substance | Inhibition Rate (%) |
| Polysaccharide | 0 |
| Core oligosaccharide of SR type | 72 |
| Core oligosaccharide of R type | 99 |

When the lipid A was used as a competitor at higher dose as much as 50 μg/ml, inhibition in ELISA was not observed. This result indicates that MH-4H7 does not bind to lipid A.

The above test revealed that MH-4H7 binds to the core oligosaccharide of R type, which lacks O-polysaccharide, and the core oligosaccharide of SR type, which possesses one repeating unit of O-polysaccharide, and therefore, the antigenic determinant (epitope) of MH-4H7 is located at the core portion of LPS of *P. aeruginosa*.

As stated in Example 5-(1), the KDO residue has been hydrolyzed by acetic acid during the process of separation of polysaccharides. Accordingly, binding of MH-4H7 to the core fraction shows that the epitope of MH-4H7 is not associated with KDO residue in the inner core portion.

EXAMPLE 6

Binding Property of Human Monoclonal Antibody MH-4H7 to LPS of Various Gram-Negative Bacteria Binding property of MH-4H7 to LPS of various Gram-negative bacteria other than *P. aeruginosa* was examined by the competitive reaction in ELISA described in Example 5-(2). As a solid antigen, 96 well microplates on which *P. aeruginosa* IID1020 cells (Type G) had been fixed were employed. The test results are shown in Table 6-(1). Intensity of the binding is shown by the inhibition rate of color development in ELISA. The concentration of the competitor was 50 µg/ml. LPSs originated from *Escherichia coli* J5, *E. coli* O111:B4, *Salmonella minnesota* R595, and *S. minnesota* wild type were obtained from List Biological Laboratories Inc., Campbell. LPSs from *P. aeruginosa* IID 1001 (Type A) and IID 1020 (Type G) were prepared by phenol extraction as illustrated in Example 4-(1).

TABLE 6-(1)

Binding Property of MH-4H7 to LPS Originated from Various Gram-Negative Bacteria (1)

| Origin of LPS | Chemotype | Concentration (µg/ml) | Inhibition Rate (%) |
|---|---|---|---|
| *E. coli* J5 | $R_c$ | 50 | 0 |
| *E. coli* O001:B4 | S | 50 | 0 |
| *S. minnesota* R595 | $R_e$ | 50 | 0 |
| *S. minnesota* wild | S | 50 | 0 |
| *P. aeruginosa* IID 1001 (Type A) | S | 50 | 91 |
| *P. aeruginosa* IID 1020 (Type G) | S | 50 | 98 |

Table 6-(1) shows that MH-4H7 does not bind to R-type LPS derived from *E. coli* J5 and *S. minnesota* R595 nor S type LPS derived from their parental strains. In view of the test results in Example 5-(2), it is concluded that the epitope of MH-4H7 is not located in LPS portion common to Enterobacteriaceae, such as inner core moiety consisting of heptose and KDO or lipid moiety, but located in outer core moiety characteristic to *P. aeruginosa*.

In accordance with the procedure as mentioned above, supplemental examination was made using other Gram-negative bacteria listed in Table 6-(2). The LPS samples used were obtained from List Biological Laboratories Inc. (Campbell) and *Pseudomonas fluorescens* was purchased from Ribi Immunochem Research Inc. (Hamilton). The LPS concentration was 50 µg/ml without exception. The test results are shown in Table 6-(2).

TABLE 6-(2)

Binding Property of MH-4H7 to LPS Originated from Various Gram-Negative Bacteria (2)

| Origin of LPS | Inhibition Rate (%) |
|---|---|
| *Escherichia coli* D31m4 | 0 |
| *Escherichia coli* K235 | 0 |
| *Escherichia coli* O26:B6 | 98 |
| *Escherichia coli* O55:B5 | 11 |
| *Escherichia coli* O127:B8 | 0 |
| *Salmonella typhimurium* | 0 |
| *Klebsiella pneumoniae* | 0 |
| *Yersinia enterocholitica* | 2 |
| *Vibrio cholerae* Inaba 569B | 0 |
| *Serratia marcescens* | 0 |
| *Pseudomonas fluorescens* | 0 |
| *Pseudomonas aeruginosa* (F-D Type 1) | 100 |

As shown in the above, MH-4H7 exerts cross reaction with LPS from *E. coli* O26:B6 strongly and with LPS from *E. coli* O55:B5 weakly, but no reaction with LPS from other bacteria. This means that the above two stains of *E. coli*, especially serotype (026) strains of *E. coli* has a chemical structure in the LPS portion common to that in the outer core moiety of the LPS of *P. aeruginosa*, which structure is capable of binding to the monoclonal antibody MH-4H7.

EXAMPLE 7

Therapeutic Effect of Antibody MH-4H7 on Experimental *P. aeruginosa* Infections in Mice Therapeutic effect of human monoclonal antibody MH-4H7 on mice experimental infections caused by clinical isolates of *P. aeruginosa*, two strains of Type A and four strains of Type G, was examined IRC-slc mice (4 week old; male; 10 animals per group) were intraperitoneally inoculated with a suspension containing the cell and 5% mutin. After one hour, the antibody MH-4H7 (0.1 µg/mouse) was administered intraperitoneally. Judgement of the therapeutic effect was made on the survival rate after one week. The test results are shown in Table 7, from which it is understood that the antibody MH-4H7 is effective in treatment of the experimental infections caused by several strains of *P. aeruginosa* of serotype A and G.

TABLE 7-(1)

Therapeutic Effect of MH-4H7 on Clinical Isolates of *P. aeruginosa* of Serotype A

| Dose µg/mouse | Survival Rate (%) (Inoculated Amount: CFU/mouse) | | | |
|---|---|---|---|---|
| | sp 6818 | | IID 1001 | |
| | $4.5 \times 10^4$ | $1.8 \times 10^5$ | $1.5 \times 10^6$ | $7.3 \times 10^6$ |
| 0.1 | 80 | 70 | 80 | 40 |
| — | 50 | 10 | 20 | 10 |

TABLE 7-(2)

Therapeutic Effect of MH-4H7 on Clinical Isolates of *P. aeruginosa* of Serotype G (1)

| Dose µg/mouse | Survival Rate (%) (Inoculated Amount: CFU/mouse) | | | |
|---|---|---|---|---|
| | sp 6788 | | sp 9701 | |
| | $3.0 \times 10^4$ | $1.2 \times 10^5$ | $1.3 \times 10^6$ | $5.1 \times 10^6$ |
| 0.1 | 100 | 90 | 100 | 90 |
| — | 30 | 0 | 60 | 20 |

TABLE 7-(3)

Therapeutic Effect of MH-4H7 on Clinical Isolates of *P. aeruginosa* of Serotype G (2)

| Dose (μg/mouse) | Survival Rate (%) (Inoculated Amount: CFU/head) | | | |
|---|---|---|---|---|
| | sp 9785 | | sp 9755 | |
| | $1.3 \times 10^6$ | $5.1 \times 10^6$ | $4.6 \times 10^3$ | $1.1 \times 10^5$ |
| 0.1 | 100 | 50 | 90 | 70 |
| — | 60 | 20 | 30 | 20 |

EXAMPLE 8

Identification of Epitope Recognized by Human Monoclonal Antibody MH-4H7

(1) Binding Property of MH-4H7 to a Group of *P. aeruginosa* Mutants Which Have Deficiency in LPS Portion Derived From *P. aeruginosa* PAC1

Epitope which is located in the outer core moiety of LPS and recognized by MH-4H7 was identified by the use of *P. aeruginosa* strains PAC 608, PAC 557, PAC 556 and PAC 611, which lack part of the outer core moiety derived from *P. aeruginosa* strain PAC1 or PAC1R which is derived from PAC1. The strains PAC1, PAC1R, and the defective mutants were obtained from Pouline M. Meadow (London University College). The strains were each coated on 96 well microplates in accordance with the disclosure in Example 2-(1), and subjected to ELISA to examine the binding activity to MH-4H7. The results are shown in Table 8-(1).

TABLE 8-(1)

Binding Property of MH-4H7 to *P. aeruginosa* Mutants which have Deficiency in Outer Core Moiety of LPS

| Strain | Chemotype | ELISA Value (OD$_{405}$) |
|---|---|---|
| PAC 1 | S | 0.30 |
| PAC 1R | S | 0.25 |
| PAC 608 | SR | 1.11 |
| PAC 557 | R | 1.13 |
| PAC 556 | R | 0.02 |
| PAC 611 | R | 0.06 |
| IID 1001* | S | 0.68 |

*Normal Control

The structures of the outer core moiety of LPSs of PAC1R and the above-mentioned mutants are known (P. S. N. ROWE & P. M. Meadow, Eur. J. Biochem., 132 329–333 (1983)). The outer core of LPS found in the parent strain, PAC1R, consists of galactosamine, alanine, glucose and rhamnose. The mutant PAC556, which showed no reaction with MH-4H7, lacks rhamnose only. Accordingly, it is concluded that the epitope of MH-4H7 is located near the rhamnose residue or the galactosamine residue to which the rhamnose residue is substituted.

(2) Binding Property of MH-4H7 to Monosaccharides and Derivatives Thereof

For the purpose of further investigation of the participation of the rhamnose residue in the epitope, binding property of MH-4H7 to monosaccharides and their derivatives was examined by the ELISA competitive reaction in accordance with Example 5-(2). As an immobilized antigen, 96 well microplates on which *P. aeruginosa* IID 1001 (Type A) was fixed were employed. Methylrhamnoside, one of the competitors used, was obtained by heating a mixture of rhamnose and methanol in the presence of 1% hydrochloric acid at 100° C. for 4 hours. Methylrhamnoside thus obtained contained about 90% α-anomer. The test results are shown in Table 8-(2).

TABLE 8-(2)

Binding Property of MH-4H7 to Monosaccharides and Derivatives Thereof

| Monosaccharide | Concentration (mM) | Inhibition Rate* (%) |
|---|---|---|
| Methyl-L-rhamnoside | 500 | 100 |
| | 50 | 22 |
| L-Rhamnose | 500 | 50 |
| | 50 | 9 |
| D-Glucose | 500 | 0 |

*Percentage of ELISA value (OD$_{405}$) presence of competitor to that in the absence of the same.

Table 8-(2) shows that MH-4H7 specifically binds to methylrhamnoside and rhamnose. Accordingly, it is decisively concluded that the epitope of MH-4H7 is deeply associated with the rhamnose reside in the outer core lipopolysaccharide of some strains of *P. aeruginosa*.

What is claimed is:

1. Human monoclonal antibody MH-4H7, secreted by the hybridoma deposited as FERM BP-2402.

2. Hybridoma MH-4H7 (FERM BP-2402) or any descendant cell line which secretes an antibody having all the same properties and characteristics of the monoclonal antibody MH-4H7.

* * * * *